(12) United States Patent
Kofol et al.

(10) Patent No.: US 7,809,434 B2
(45) Date of Patent: Oct. 5, 2010

(54) SYSTEM AND METHOD FOR EEG IMAGING OF CEREBRAL ACTIVITY USING SMALL ELECTRODE SETS

(75) Inventors: Tim Kofol, Boston, MA (US); Scott D. Greenwald, Norfolk, MA (US); Philip H. Devlin, Brookline, MA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1338 days.

(21) Appl. No.: 11/294,321

(22) Filed: Dec. 5, 2005

(65) Prior Publication Data

US 2006/0149160 A1    Jul. 6, 2006

Related U.S. Application Data

(60) Provisional application No. 60/632,762, filed on Dec. 3, 2004.

(51) Int. Cl.
*A61B 5/04* (2006.01)
(52) U.S. Cl. ...................................... 600/544; 600/545
(58) Field of Classification Search .................. 600/544, 600/545
See application file for complete search history.

(56) References Cited

U.S. PATENT DOCUMENTS

| 4,736,751 | A |  | 4/1988 | Gevins et al. |
| 4,862,359 | A |  | 8/1989 | Trivedi et al. |
| 5,119,816 | A |  | 6/1992 | Gevins |
| 5,331,970 | A | * | 7/1994 | Gevins et al. ............... 600/544 |
| 5,568,816 | A |  | 10/1996 | Gevins et al. |

OTHER PUBLICATIONS

Pascual-Marqui, R.D. et al., *International Journal of Psychophysiology*, vol. 18, pp. 49-65, 1994.
Pizzagalli, D. et al., "Anterior Cingulate Activity as a Predictor of Degree of Treatment Response in Major Depression: Evidence from Brain Electrical Tomography Analysis", *American Journal of Psychiatry*, vol. 158:3, pp. 405-415, Mar. 2001.

* cited by examiner

*Primary Examiner*—Robert L Nasser
*Assistant Examiner*—Michael D'Angelo

(57) ABSTRACT

The invention provides a method of estimating cerebral sources of electrical activity from a small subset of EEG channels utilizing existing methods to provide a 3-dimensional, discrete, distributed, linear solution to the inverse problem using inputs consisting of a small number of EEG channels (e.g., 4 channels) augmented with synthetic EEG data for the other channels. The resultant image of cerebral electrical activity in the region of the EEG channels from which data is recorded is of comparable spatial resolution in the corresponding region to images of cerebral electrical activity obtained using a complete set of EEG channels (e.g., using 24 channels).

20 Claims, 5 Drawing Sheets

SYSTEM AND METHOD FOR EEG IMAGING OF CEREBRAL ACTIVITY USING SMALL ELECTRODE SETS

CROSS REFERENCE TO RELATED APPLICATION

This application claims priority from U.S. Provisional Application Ser. No. 60/632,762 filed on Dec. 3, 2004.

BACKGROUND

The electroencephalogram (EEG) is a record of the electrical voltage signal recorded on the scalp. The EEG is in reality the summated electrical activity of the billions of neurons which make up the brain. In order to study the electrical activity of the brain, a simplified model may be utilized which considers the EEG to be produced by a relatively small number of current sources located in the brain, which is considered to be a volume conductor. The problem of identifying unknown internal current sources within a volume conductor from a known set of voltage measurements on the surface of the volume is called the "inverse problem." (The "forward problem" is the process of estimating voltages on a surface given known sources of electrical activity within a volume.) There are a number of methods for providing solutions to the inverse problem used in both cardiology (linking the electrocardiogram or ECG with the heart) and neurology (linking EEG with the brain). Because the inverse solution is not unique, approximations are estimated using a set of assumptions and constraints regarding the sources. For purposes of this invention, we shall use the term "Inverse Method" as a generic name for an analytical tool that takes a large set of voltage measurements (spatially distributed around the source organ) and estimates the source properties. Therefore, given a set of EEG signals collected simultaneously from the scalp of a subject, an Inverse Method can be used to calculate the underlying cerebral electrical activity which generated the EEG data, given a set of mathematical constraints. One commonly used Inverse Method is Low Resolution Brain Electromagnetic Tomography (LORETA) as described in "Low resolution electromagnetic tomography: a new method for localizing electrical activity in the brain," Pascual-Marqui R D, Michel C M, Lehmann D. International Journal of Psychophysiology 1994, 18:49-65.

Clinicians often image the brain, focusing on particular regions of interest to aid in the diagnosis of particular abnormalities. A wide variety of algorithms and mathematical models have been developed to derive images of brain activity from EEG signals recorded from scalp electrodes (see, for example, U.S. Pat. Nos. 4,862,359 and 4,736,751). EEG imaging of the brain, as it is generally implemented in research studies, typically requires large, multi-channel, full-head electrode montages which are impractical in many clinical settings. Such techniques typically use at least 19 channels of EEG data, and more usually 24 channels. Without these large electrode sets, the spatial detail in the resultant image becomes poor and provides little information to the clinician.

The clinical application of such techniques is limited, however, in part due to the time-consuming and technically difficult need to apply 19-24 electrodes over the entire scalp of a patient. In addition, EEG recording devices which simultaneously collect large numbers of channels are expensive and complex, due to the need to provide a large number of high-fidelity channels. For this reason, it would be desirable to obtain EEG images using smaller data sets without the loss of spatial resolution, the usual trade-off for smaller number of channels. There are various reported methods of improving spatial detail of EEG-derived images based on anthropomorphic data as well as measurements of electrodes position, scalp and skull thickness, as well as brain shape; see for example U.S. Pat. No. 5,568,816 issued to Gevins et al. entitled "EEG Deblurring Method and System for Improved Spatial Detail" and U.S. Pat. No. 5,331,970 issued to Gevins et al. for "EEG Spatial Enhancement Method & System". However, in the case in which an inverse solution is applied to a limited set of EEG channels (e.g., 4 channels), these methods cannot provide sufficient spatial resolution to be useful in a clinical application.

It is therefore an object of the present invention to provide EEG-derived images of comparable resolution in a particular region using a small subset of EEG channels to those derived using a full set of EEG channels.

SUMMARY OF THE INVENTION

The invention provides a method of estimating cerebral sources of electrical activity from a small subset of EEG channels utilizing existing methods to provide a 3-dimensional, discrete, distributed, linear solution to the inverse problem using inputs consisting of a small number of EEG channels (e.g., 4 channels) augmented with synthetic EEG data for the other channels. The resultant image of cerebral electrical activity in the region of the EEG channels from which data is recorded is of comparable spatial resolution in the corresponding region to images of cerebral electrical activity obtained using a complete set of EEG channels (e.g., using 24 channels).

DETAILED DESCRIPTION OF THE PREFERRED EMBODIMENTS

Figure 1:
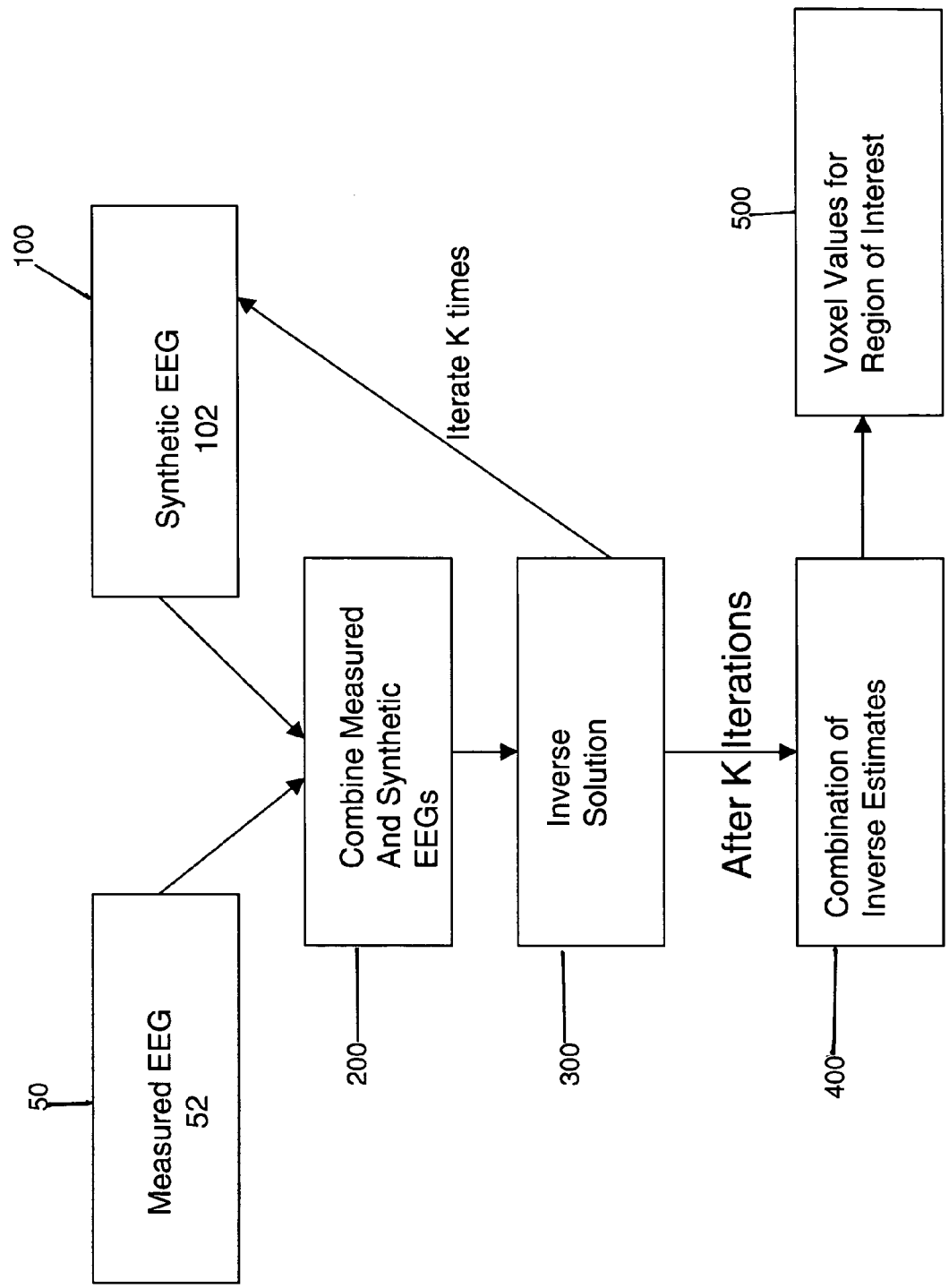
FIG. 1 is a schematic block diagram of the method of the present invention.

The method of the present invention is shown in FIG. 1. The method estimates cerebral sources of electrical activity for a set of N input channels of EEG data utilizing Inverse Methods well known in the art. The N input channels consist of M channels of acquired (measured) EEG data augmented with synthetic EEG data for the remaining (N−M) channels, where M<N. As shown herein, there are 5 main steps in this process:

1. Acquiring M channels of EEG data representative of cerebral activity of a patient in step 50. The measured EEG signals are acquired by means of one or more EEG electrodes and amplifiers or other known EEG processing components, to produce a channel of measured EEG data;
2. Creating K sets of N−M channels of synthetic EEG data in step 100 corresponding to the "missing" channels;

3. Combining the M measured channels with the K sets of N–M synthetic EEG channels in step 200;
4. For each combination of measured channels and one of the K sets of synthetic data, calculating the inverse solution using an Inverse Method utilizing the combined set of N channels in step 300;
5. Repeating steps 100, 200 and 300 K times and combining the results from K inverse solutions to create the final inverse solution in step 400.

The final inverse solution does not provide high spatial resolution voxel values for the entire brain. Instead, the region of high spatial resolution is specific to a particular region of interest that is determined by the positioning of the measured electrodes and the methods used to combine the inverse solutions.

A set of one or more EEG electrodes are applied to the specific regions of interest. The electrodes are generally positioned in the standard locations specified in the International 10/20 system, although other electrode positions may be used without impacting the performance of the invention. EEG signals are collected from each of these electrodes in a fashion well known in the state of the art. Generally, the signal is obtained from each electrode using an amplifier. The acquired signal may be filtered using physical (electronic) or software filters to reduce the effect of noise and artifact upon the EEG signal. Each signal so collected from each of the set of electrodes is referred to as a measured EEG channel that is used in step 50. The measured EEG is preferably acquired at a sampling rate of 128 samples per second and is stored in the memory of a processor in 2 second lengths referred to as buffers, each containing 256 samples. Other sampling rates and buffer lengths may be used without affecting the operation of the algorithm, though these would affect the frequency resolution of the resulting image.

The synthetic EEG 102 used in step 100 may be generated by a number of methods. In the preferred embodiment, synthetic EEG is generated from a database of measured EEG signals from previously collected normal patients (i.e. those having no cognitive dysfunction or abnormality). The database of normal EEG signals contains only artifact-free segments of data. In addition, it is important that the synthetic EEG signals 102 be of equal or greater length than the measured EEG 52 to facilitate an effective application of the correlation operation of the combination process. The preferred buffer length of the synthetic data is 12.5% longer than that of the measured data, or 2.25 seconds in the preferred embodiment. The sampling rate of the synthetic data must also be at the same rate as that of the measured data, such that the synthetic EEG buffer in the preferred embodiment contains 320 samples.

Another method of synthetic EEG generation that can be used for this invention is the use of a database of previously measured EEG signals from the same patient. Alternatively, synthetic EEG may also be generated by a number of other methods including: use of EEG created from forward solution models using model parameters derived from a database of normal subjects, prediction of EEG using the combination of the M measured signals and information about the spatial distribution of the M and N–M electrode sets, and signals that would provide power uncorrelated with the measured EEGs (e.g., sinusoids, isoelectric signals, white noise, etc.). In addition, synthetic EEG may be created by any combination of the previously stated synthetic EEG types. All such methods will have specific strengths and weaknesses and are included as specific alternate embodiments of the invention.

Figure 2:
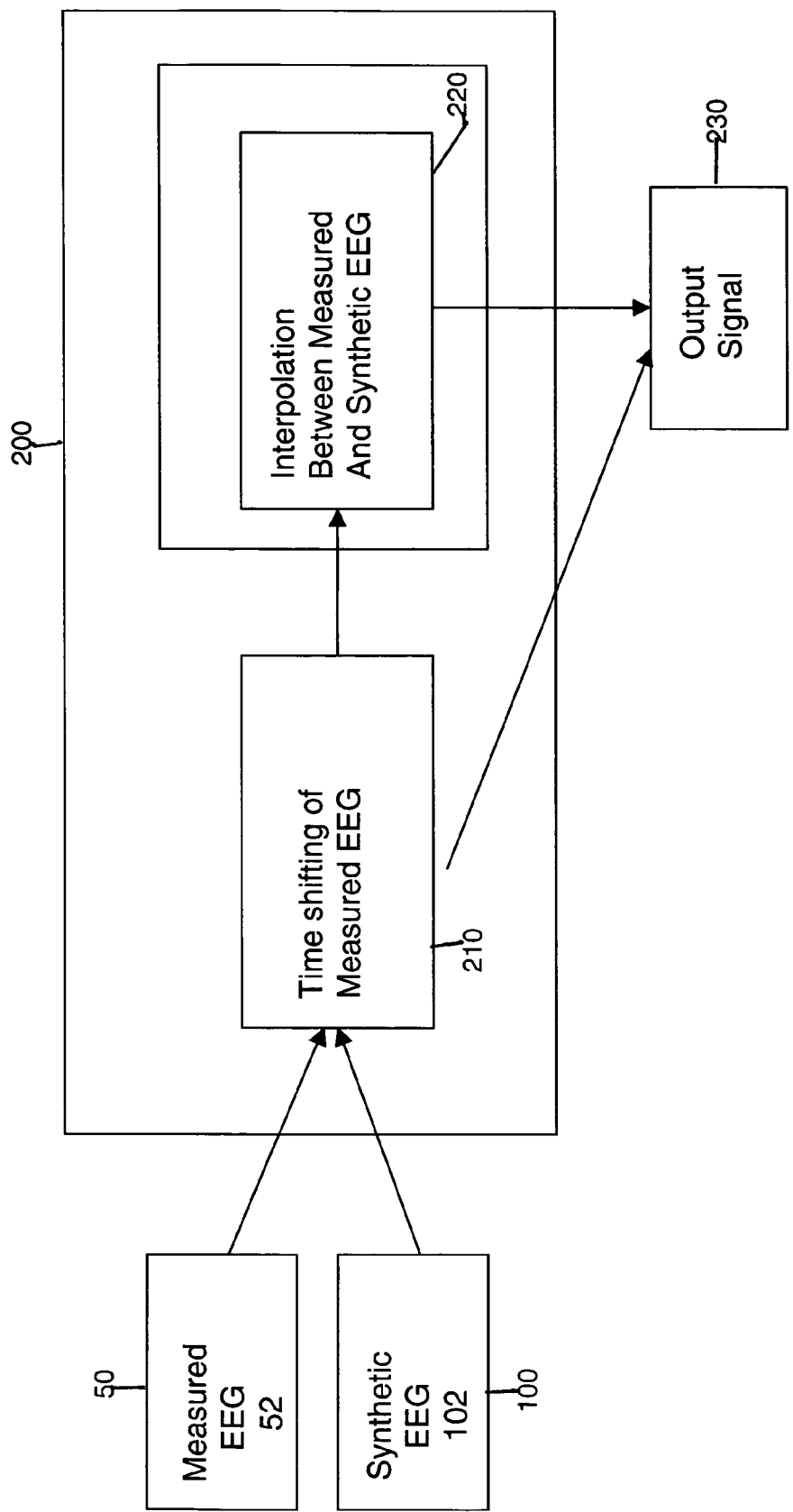
FIG. 2 is a schematic block diagram of the method combining synthetic and measured EEG signals of the present invention.

Turning now to FIG. 2, the process of combining the measured and synthetic EEG signals of step 200 receives two inputs consisting of N channels of EEG signals, the measured EEG signals 52 and the synthetic EEG signals 102. Each of the measured EEG signals 52 and synthetic EEG signals 102 consists of a set of channels, where each of the M measured EEG channels is a signal derived from an individual EEG electrode and each of the N–M synthetic channels is a separate unique EEG signal. In general, the operation of the process of combining will be described by considering the EEG buffers as a set of data points, $EEGM_k(i)$ for the measured EEG signals 52 and $EEGS_k(i)$ for the synthetic EEG signals 102, where i is the index of an individual sample within the buffer and k is the channel number.

The combination process 200 compares the two sets of EEG signals, measured EEG signals 52 and synthetic EEG signals 102 and time shifts such signals in step 210 and interpolates such time shifted signals in step 220 so that the synthetic EEG signals 102 are more similar to EEG signals 52 that would have been acquired if all the EEG channels were measured. The time shift process 210 will be described first.

In order to time shift the data, the buffer length of the measured EEG signal 52 must be shorter than the buffer length of the synthetic EEG signal 102. The time shift process will function mathematically if the buffer of the measured EEG signal 52 is at least one sample shorter than that of the synthetic EEG signal 102. However, the best performance will be obtained when the buffer length LS of the synthetic EEG signal 102 is significantly longer than the buffer length LM of the measured EEG signal 52, 12.5% longer in the preferred embodiment. Therefore in the preferred embodiment, $LS=1.25*LM$.

The time shift process 210 shifts the synthetic data in time (i.e., to the left or right with respect to the measured data) in such a manner as to maximize the overall correlation between the measured EEG signals 52 and the synthetic EEG signal 102. It is possible however, through the action of chance, to obtain synthetic data which is identical to the measured data or nearly so, though perhaps time-shifted. If such a synthetic data channel were time shifted, the resultant set of EEG data would contain two data channels (one measured and one synthetic) with very high interchannel correlation. This would effectively reduce the number of statistically independent EEG channels in the overall data set, since one of the highly-correlated channels would in effect be a linearly scaled version of the other. This high level of interchannel covariance may result in difficulties in subsequent analysis of the combined EEG channels produced by the invention, since many methods of analysis make the mathematical assumption that the channels of EEG are statistically independent. It is therefore necessary to limit the interchannel EEG correlation which is obtained through the operation of the time shift process to some maximum value. In the preferred embodiment, the correlation of all possible pairs of non-time-shifted measured EEG channels is calculated, and the maximum of these measured interchannel correlations is used as the maximum allowable interchannel correlation in the time-shifted data.

There are many well-known methods of computing correlation coefficients in the art. In the preferred embodiment, the Pearson correlation is used, although other methods, such as the Spearman rank correlation may be used without loss of generality of the process. In general, the Pearson correlation between two measured EEG channels a and b is $$R_{ab} = \frac{LM\left(\sum_{i=1}^{LM} EEGM_a(i)EEGM_b(i)\right) - \left(\sum_{i=1}^{LM} EEGM_a(i)\right)\left(\sum_{i=1}^{LM} EEGM_b(i)\right)}{\sqrt{\left[LM\sum_{i=1}^{LM} EEGM_a^2(i) - \left(\sum_{i=1}^{LM} EEGM_a(i)\right)^2\right]\left[LM\sum_{i=1}^{LM} EEGM_b^2(i) - \left(\sum_{i=1}^{LM} EEGM_b(i)\right)^2\right]}}$$

The maximum allowable interchannel correlation is thus $$RMAX = \max(R_{ab})$$

where a=1, 2, 3 ... M, b=1, 2, 3 ... M, a≠b. To speed the implementation, it should be noted that $R_{ab}=R_{ba}$ and thus only one of the pair $R_{ab}$, $R_{ba}$ need be computed.

Figure 3:
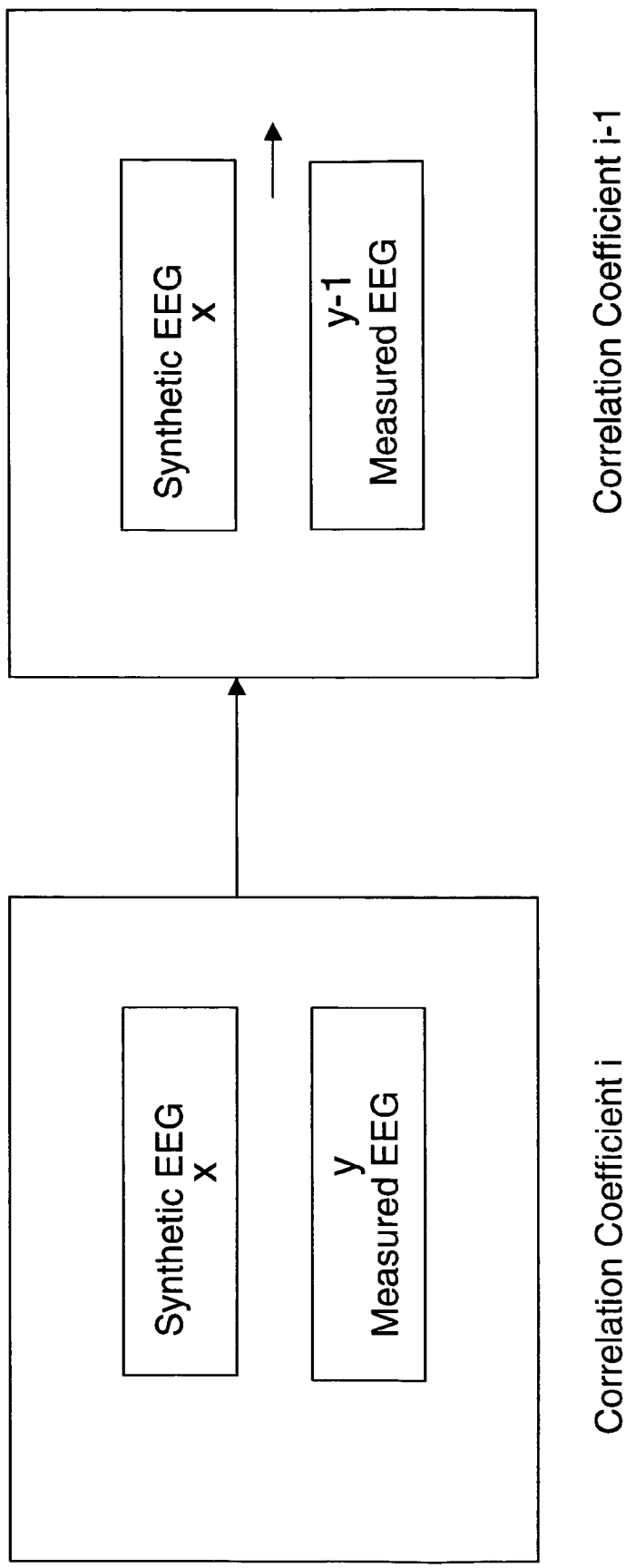
FIG. 3 is a schematic block diagram of the process for time shifting the measured EEG used in the present invention.

The time shift process 210 next calculates the correlation between every measured EEG channel and every synthetic EEG channel, for every time alignment between the measured and synthetic EEG buffers that provides LM sample pairs. This is illustrated in FIG. 3, in which the first correlation coefficient A is computed as the correlation between the synthetic EEG buffer and the (unshifted) measured EEG buffer, aligned so that the measured EEG buffer sample x is aligned with the synthetic EEG buffer sample y. The measured EEG is then shifted by one sample so that measured EEG buffer sample x is aligned with the synthetic EEG buffer sample y-1, and the correlation calculation is again performed. This will continue for a total of (LS−LM+1) calculations and will create an array of (LS−LM+1) correlation coefficients, for each pair of measured and synthetic EEG channels. The samples of the synthetic EEG buffer that are not aligned with a sample of the measured EEG buffer (due to greater number of samples in the synthetic EEG buffer) are not used in the correlation calculation.

$$\{R_{ab}(j)\} = \frac{LM\left(\sum_{i=1}^{LM} EEGM_a(i-j)EEGS_b(i)\right) - \left(\sum_{i=1}^{LM} EEGM_a(i-j)\right)\left(\sum_{i=1}^{LM} EEGS_b(i)\right)}{\sqrt{\left[LM\sum_{i=1}^{LM} EEGM_a^2(i-j) - \left(\sum_{i=1}^{LM} EEGM_a(i-j)\right)^2\right]\left[LM\sum_{i=1}^{LM} EEGS_b^2(i) - \left(\sum_{i=1}^{LM} EEGS_b(i)\right)^2\right]}}$$

where a=1, 2, 3 ... M, b=1, 2, 3 ... (M−N) and j=0, 1, 2 ... (LS−LM). The beginning index value i is 1 in both the buffers EEGM and EEGS. Note that here, $R_{ab} \neq R_{ba}$ and thus both $R_{ab}$ and $R_{ba}$ need to be computed.

The correlation arrays $\{R_{ab}(j)\}$ are combined over all the channel pairs a, b to create a single composite correlation array R(j) of length (LS−LM+1). In the preferred embodiment, the arithmetic mean is used as the combination function, although other combination functions known in the art may be used in alternate embodiments. These include, but are not limited to, medians, trim-means, trim-medians, centroids, etc. The composite correlation array R(j) is calculated as $$R(j) = \frac{1}{M(N-M)} \sum_{a=1}^{M} \sum_{b=1}^{M-N} R_{ab}(j)$$

where j = 0, 1, 2 ... (LS − LM).

The process finds the maximum value of R(j) that is less than or equal to the maximum allowable interchannel correlation RMAX; the value of j at the point of this allowable maximum, $j_{max}$, is the time shift corresponding to the maximum allowable correlation.

$$R(j_{max}) = \max(R(j)); j = 0, 1, 2 \ldots (LS-LM).$$

such that $$R(j_{max}) \leq RMAX$$

The time shift process 210 then shifts each of the synthetic EEG buffers by $j_{max}$ samples.

$$EEGSshift_k(i) = EEGS_k(i-j_{max})$$

where k=1, 2, 3 ... M and i=1, 2, ... LM. This produces a shifted synthetic EEG buffer of length; the additional samples of the synthetic EEG buffer that do not align with a corresponding sample of the measured EEG buffer are dropped. Again, other correlation metrics (Spearman rank correlation, etc) and measures of association may be used in place of the Pearson correlation without loss of generality of the algorithm.

Referring to FIG. 2, the interpolation process 220 will be described. In the preferred embodiment, the interpolation process 220 is not applied if the synthetic EEG is derived from actual EEG, such as measured EEG data obtained from a database of normal patients or previously recorded measured EEG data from the same subject. If the synthetic EEG is not similar to human EEG (such as white noise, sinusoidal signals, etc.), the synthetic EEG is interpolated using the physical distance $d_{ab}$ (in millimeters) on the subject's scalp between the electrode site corresponding to the synthetic EEG channel currently being interpolated $EEGS_a$ and the electrode site corresponding to the measured EEG channel, $EEGM_b$.

For every sample i in the buffer corresponding to synthetic EEG channel $EEGSshift_a(i)$, a value $X_a(i)$ is added to it to produce the interpolated synthetic EEG channel $EEGSin_a(i)$, $$EEGSin_a(i) = EEGSshift_a(i) + X_a(i)$$

$$X_a(i) = S_a Y \sum_{k=1}^{M} \frac{EEGM_k(i)}{d_{ak}^2}$$

where a=1, 2 ... (N−M) and i=1, 2 ... LM.

The constant Y is an interaction factor, the value of which controls the extent to which the measured EEG signals 52 influence the synthetic EEG signals 102. In general, Y is a user-specified value and is set to 6.5 in the preferred embodiment. While the interaction factor Y is constant for all regions in the preferred embodiment, different values of Y may be used for different scalp regions or electrode sets. Furthermore, a scaling factor $S_a$ may be applied to the synthetic or measured EEG, the scaling factor being dependent on the EEG channels being used and the region of interest within the brain. The scaling factor is used to preferentially weight specific EEG channels or regions more heavily than others.

The set of the measured EEG channels $EEGM_k$, k=1, 2 ... M and the shifted interpolated synthetic EEG channels EEG-$Sin_a$, a=1, 2 ... (N−M) constitute the set of N output channels 230 from the combination process 200. This set of output channels is used as the input to the inverse solution process 300. Source localization and the inverse solution for EEG signals are discussed in U.S. Pat. Nos. 5,119,816, 5,568,816 and 5,331,970. A similar solution to the source localization problem LORETA is used in this invention. This LORETA inverse solution is iterated K times. K can be defined as any integer number greater than zero. The larger the value of K, the smaller the confidence interval surrounding the final estimate of the inverse solution. It is preferable to set K to be as large as possible, given the constraints of processing capacity and thus time required to obtain a result. In the current invention, K is set equal to 50 iterations. This provides an adequate compromise between the variance of the estimate of the inverse solution and the time required to obtain a solution.

Referring now to FIG. 1, for each of the K iterations, a different set of synthetic EEG data 102 is used in combination with the original set of measured EEG data 52. At each iteration, the combination process 200 is applied to the measured and synthetic data, consisting of the time shift process 210 and the interpolation process 220. Thus, given a total of N input channels, consisting of M measured channels and N−M synthetic channels, for each iteration a unique set of N−M time-shifted, interpolated synthetic channels of data and M channels of measured data are calculated. The output of the inverse solution 300 is a voxel image for the region of interest. After K iterations, there exist K voxel images of the region of interest. In the preferred embodiment, these images from the K inverse solutions are combined using an arithmetic average of the corresponding voxels in each image as the combination function. Depending on the distribution of the voxels, other combination functions may be more appropriate. Other methods to be considered based on the distribution of the voxel images include medians, trim-means and weighted averages.

Once the final combined voxel image (inverse solution) 500 is calculated, the voxel estimates of the current densities can be displayed for visual interpretation or can be manipulated to provide clinically relevant information for a region of interest. For example, metabolic rate of the prefrontal anterior cingulate cortex (ACC) has been shown to be a predictor of response to antidepressant treatment as taught by "Anterior Cingulate Activity as a Predictor of Degree of Treatment Response in Major Depression: Evidence from Brain Electrical Tomography Analysis," Pizzagalli D, Pascual-Marqui R D, Nitschke J, Oakes T, Larson C, Abercrombie H,. 2001. American Journal of Psychiatry 2001, 158:405-415. Prior work has demonstrated that LORETA estimates of the ACC current density correlate with metabolic rate. We have identified one candidate subset of EEG channels (i.e., F7-Fpz, F8-Fpz, A1-Fpz, and A2-Fpz) that, when combined with synthetic data, are sufficient to estimate current density in this ACC region. Thus, clinicians may find a 4-channel EEG system clinically useful for estimating metabolic activity of the prefrontal ACC, and consequently, for managing antidepressant therapy.

Example: The above technique was used to image the theta activity of the anterior cingulate from 4 electrode pairs in a set of 25 depressed subjects (F7-Fpz, F8-Fpz, A1-Fpz, and A2-Fpz, using electrode site notation from the 10/20 International System). Using the original set of 24 channels of acquired EEG data for these depressed subjects, it was found that medication responders had higher current density in the prefrontal anterior cingulate cortex related to EEG theta activity (4-8 Hz) compared to non-responders (p<0.05). We found that it was possible to recreate these results using 4 EEG channels if the proper parameters were applied to the above stated method. The synthetic data used for the 20 (i.e., 24-4) channels was EEG acquired from a second population consisting of 10 non-depressed, normal subjects. The EEG amplitude of the EEG from the normal subjects was scaled by 1/1.75 to reduce its contribution to theta activity relative to the 4 channels of EEG data measured from the depressed subjects. The inverse transform (using LORETA) was then applied to the combined 24 channels of EEG data. This process was repeated 10 times per depressed subject, once for each combination of 4 channels of EEG data from the depressed subjects with 20 channels of EEG from each normal subject. The final inverse solution for each depressed subject was derived from the average of the corresponding 10 inverse solutions.

Figure 4:
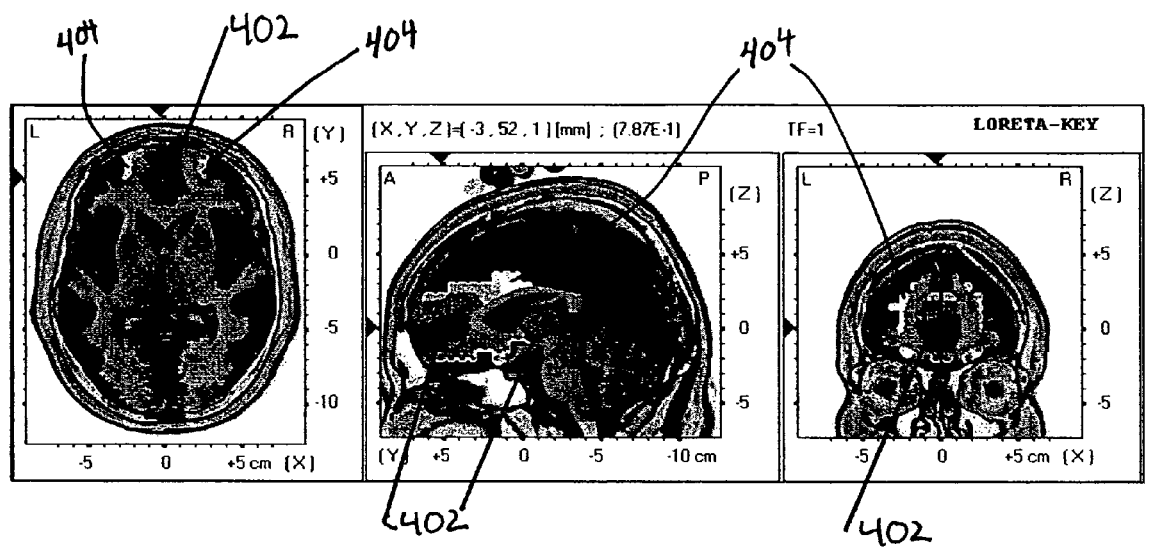
FIG. 4 is a view of an image of the brain showing the distribution of correlation coefficients between standard and novel methods.

Correlation between estimates of voxel current intensities between the 2 methods (i.e., Standard Method using the original 24 channels vs. Novel Method using 4 channels from the depressed subject plus 20 channels of synthetic EEG) was used to evaluate the performance of Novel Method in estimating the current intensities of the prefrontal ACC. The pictorial results are shown in FIG. 4. The white zone 404 contained voxels where the method-to-method correlation was less than 0.4. The dark regions 402 contained voxels where the correlation between methods exceeded 0.8. These results demonstrate that there is a significant correlation between methods in the region of interest.

Figure 5:
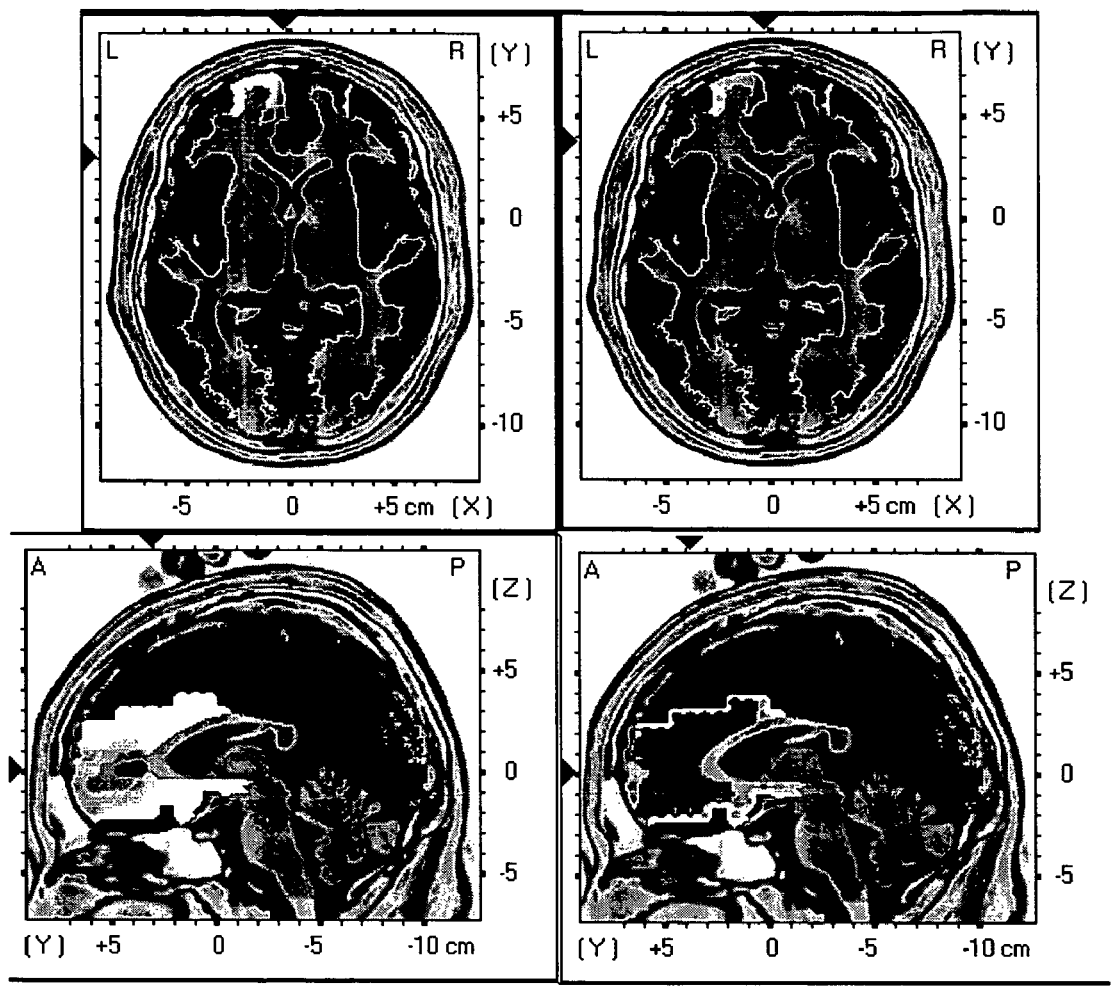
FIG. 5 is a view of the resulting images of the brain of the comparison of regions used in the present invention that were statistically significantly different between medication responders and non-responders.

To evaluate the clinical relevance of this technology, both methods were used to estimate current densities in the prefrontal ACC in a group of depressed patients prior to treatment with reboxetine. Group analysis compared ACC activity between responders and non-responders, and FIG. 5 shows that both methods identified responders as having statistically lower intensity (i.e., lower metabolism) in this region. The left column contains results for the Novel Method (using 4 channels of EEG from the depressed subjects); the right column contains results from the Standard Method (using 24 channels of EEG from the depressed subjects). The top row is a coronal section containing the ACC. The bottom row is a sagittal view containing the ACC. Darker regions represent areas of greater difference in estimated current density between medication responder and non-responder groups.

While the foregoing invention has been described with reference to its preferred embodiments, various alterations and modifications will occur to those skilled in the art. All such modifications and alterations are intended to fall within the scope of the appended claims.

We claim:

1. A method of estimating cerebral sources of electrical activity from a set of EEG channels comprising the steps of:
   obtaining M channels of measured EEG signal data and N−M channels of synthetic EEG signal data, where M<N;
   creating sets of N−M channels of synthetic EEG signal data; and
   calculating, using a processor, an inverse solution from a combination of said sets of N−M channels of EEG signal data and said M channels of EEG signal data.

2. The method of estimating cerebral sources of electrical activity of claim 1 further comprising the step of calculating a final inverse solution by repeating said step of calculating an inverse solution from a combination of said sets of N−M channels of synthetic EEG signal data and said M channels of measured EEG signal data.

3. The method of estimating cerebral sources of electrical activity of claim 1 further comprising the step of combining said M channels of measured EEG signal data with said sets of N–M channels of synthetic EEG signal data.

4. The method of estimating cerebral sources of electrical activity of claim 3 wherein said step of combining comprises the steps of:
   time shifting said sets of N–M channels of synthetic EEG signal data to maximize the overall correlation between said M channels of measured EEG signal data and said N–M channels of synthetic EEG signal data; and
   correlating each of said M channels of measured EEG signal data and each of said N–M channels of synthetic EEG signal data.

5. The method of estimating cerebral sources of electrical activity of claim 1 further comprising 4 channels of measured EEG signal data and 20 channels of synthetic EEG signal data.

6. The method of estimating cerebral sources of electrical activity of claim 1 further comprising generating an image of cerebral electrical activity in a brain region based at least in part on the inverse solution.

7. The method of estimating cerebral sources of electrical activity of claim 1 wherein creating sets of N–M channels of synthetic EEG signal data comprises accessing a database of previously collected EEG signal.

8. A method of estimating cerebral sources of electrical activity from a set of EEG channels comprising the steps of:
   obtaining M channels of measured EEG signal data and N–M channels of synthetic EEG signal data, where M<N;
   creating sets of N–M channels of synthetic EEG signal data;
   calculating an inverse solution from a combination of said sets of N–M channels of EEG signal data and said M channels of EEG signal data; and
   generating an image of cerebral electrical activity in a brain region based at least in part on the inverse solution.

9. The method of estimating cerebral sources of electrical activity of claim 8 further comprising the step of calculating a final inverse solution by repeating said step of calculating an inverse solution from a combination of said sets of N–M channels of synthetic EEG signal data and said M channels of measured EEG signal data.

10. The method of estimating cerebral sources of electrical activity of claim 8 further comprising the step of combining said M channels of measured EEG signal data with said sets of N–M channels of synthetic EEG signal data.

11. The method of estimating cerebral sources of electrical activity of claim 10 wherein said step of combining comprises the steps of:
   time shifting said sets of N–M channels of synthetic EEG signal data to maximize the overall correlation between said M channels of measured EEG signal data and said N–M channels of synthetic EEG signal data; and
   correlating each of said M channels of measured EEG signal data and each of said N–M channels of synthetic EEG signal data.

12. The method of estimating cerebral sources of electrical activity of claim 8 further comprising 4 channels of measured EEG signal data and 20 channels of synthetic EEG signal data.

13. The method of estimating cerebral sources of electrical activity of claim 8 wherein creating sets of N–M channels of synthetic EEG signal data comprises accessing a database of previously collected EEG signal data.

14. A system for estimating cerebral sources of electrical activity from a set of EEG channel, the system comprising:
   EEG sensors capable of obtaining M channels of measured EEG signal data and N–M channels of synthetic EEG signal data, where M<N;
   A processor capable of:
      creating sets of N–M channels of synthetic EEG signal data; and
      calculating an inverse solution from a combination of said sets of N–M channels of EEG signal data and said M channels of EEG signal data.

15. The system of claim 14 further capable of calculating a final inverse solution by repeating said step of calculating an inverse solution from a combination of said sets of N–M channels of synthetic EEG signal data and said M channels of measured EEG signal data.

16. The system of claim 14 further capable of combining said M channels of measured EEG signal data with said sets of N–M channels of synthetic EEG signal data.

17. The system of claim 16 further capable of:
   time shifting said sets of N–M channels of synthetic EEG signal data to maximize the overall correlation between said M channels of measured EEG signal data and said N–M channels of synthetic EEG signal data; and
   correlating each of said M channels of measured EEG signal data and each of said N–M channels of synthetic EEG signal data.

18. The system of claim 14 further comprising 4 channels of measured EEG signal data and 20 channels of synthetic EEG signal data.

19. The system of claim 14 further comprising a display capable of displaying an image of cerebral electrical activity in a brain region based at least in part on the inverse solution.

20. The system of claim 14 further capable of accessing a database of previously collected EEG signal to create the sets of N–M channels of synthetic EEG signal data.

* * * * *